United States Patent [19]
Lawson

[11] 4,085,024
[45] Apr. 18, 1978

[54] GALVANIC CELL ASSEMBLY FOR DETECTING OXYGEN AND METHOD OF MAKING SAID CELL

[75] Inventor: Thomas E. Lawson, Denver, Colo.

[73] Assignee: Lexington Instrument Corporation, Waltham, Mass.

[21] Appl. No.: 717,771

[22] Filed: Aug. 26, 1976

[51] Int. Cl.² ............................................. G01N 27/46
[52] U.S. Cl. .............................. 204/195 R; 29/592 R; 29/623.1; 204/1 T
[58] Field of Search .............. 204/14, 195 R; 324/29; 29/592, 595

[56] References Cited
U.S. PATENT DOCUMENTS

| 3,223,597 | 12/1965 | Hersch | 204/1 Y |
| 3,793,158 | 2/1974 | Hamilton | 204/1 Y |

FOREIGN PATENT DOCUMENTS 1,151,911   5/1969   United Kingdom ................... 324/29

Primary Examiner—G. L. Kaplan
Attorney, Agent, or Firm—Robert T. Dunn

[57] ABSTRACT

The electrode assembly of a galvanic cell for detecting and measuring small amounts of oxygen absorbed by the assembly is a symmetrical sandwich mounted on an anode plate or blade and including contiguous with the blade on each side thereof a porous anode carrying an anode material such as cadmium covered with a sheet of non-reticulated, porous, non-conductive, electrolyte retentive material wrapped around the blade, a cathode conductor strip wrapped around the sheet of electrolyte retentive material, a sheet of porous cathode material, such as graphite cloth wrapped around that and secured in place and the assembly is immersed in electrolyte, electrically charged and sealed inside an oxygen-free envelope.

24 Claims, 9 Drawing Figures

U.S. Patent          April 18, 1978          4,085,024
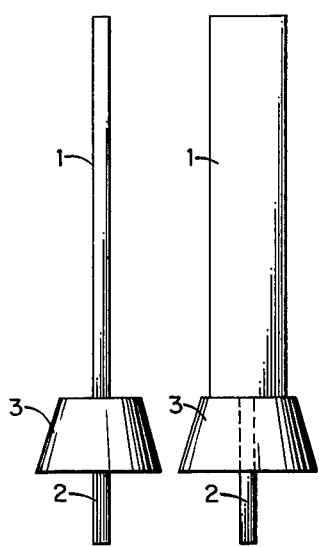
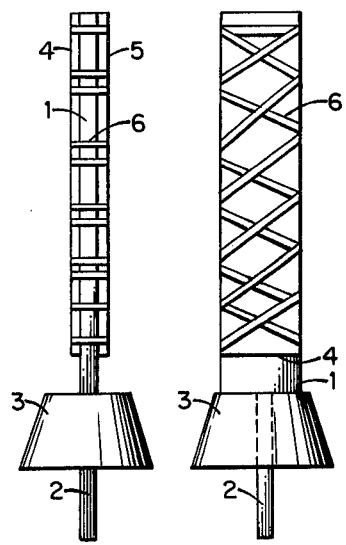
Fig. 1.    Fig. 2.    Fig. 3.    Fig. 4.
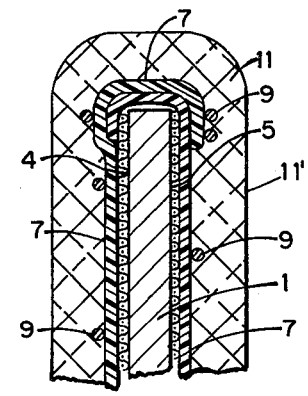
Fig. 9.
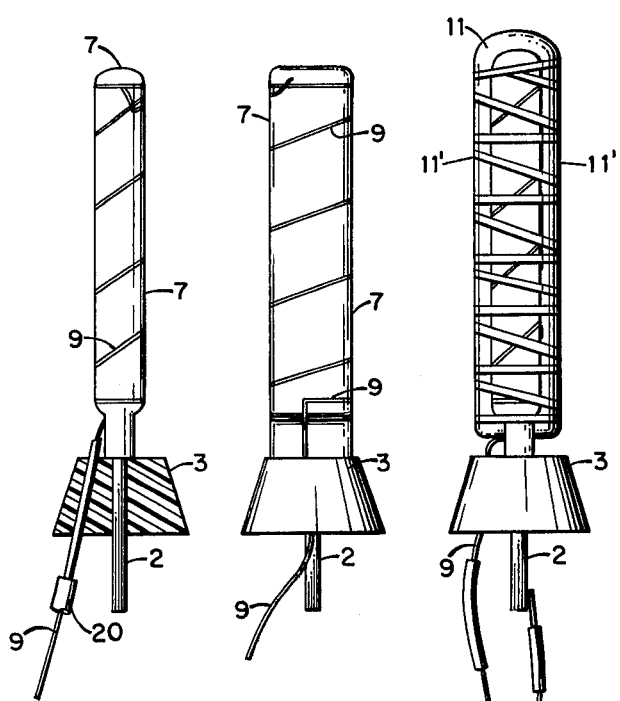
Fig. 5.    Fig. 6.    Fig. 7.
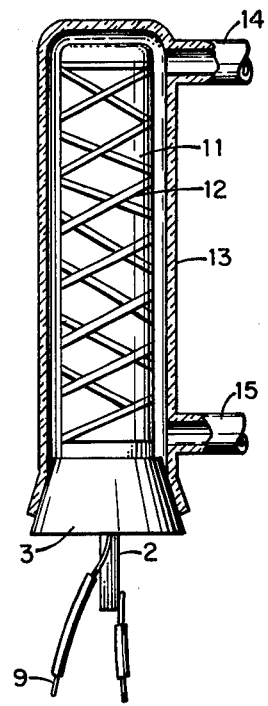
Fig. 8.

GALVANIC CELL ASSEMBLY FOR DETECTING OXYGEN AND METHOD OF MAKING SAID CELL

BACKGROUND OF THE INVENTION

The present invention relates to a method and means of construction of a galvanic cell used for the detection and measurement of small quantities of oxygen which are absorbed by the cell.

Heretofore, galvanic cells have been used to measure small amounts of oxygen introduced to the cell in gaseous form. The cell includes an anode and a cathode separated by a non-conductive, porous material that retains electrolyte and is sometimes called the diaphragm. The assembly is dampened with an electrolyte so that a precise amount of the electrolyte is absorbed in the diaphragm and then the assembly is placed in a sealed oxygen-free envelope. Some of the material suggested for use as the anode include cadmium, arsenic, bismuth, antimony, lead and ferrous hydrate. Some of the materials suggested for use as the cathode include silver, gold, platinum, copper, iridium and carbon. When a small amount of oxygen is introduced into the envelope, it is aborbed by the cathode and becomes ionized. The ions of oxygen migrate through the electrolyte to the anode and oxidize the anode material giving up electrons to the anode and these electrons flow through an external circuit path that is provided. Generally, the lower the external circuit path resistance, the faster will be the action of the cell. After the anode material becomes largely oxidized, the cell loses efficiency and its action slows down. The cell can be revitalized by applying a current to it (plus to the cathode and minus to the anode) and at the same time venting the cell to carry off the evolved oxygen.

In the past, the cell sensitivity to even very minute amounts of oxygen was improved using a porous cathode in combination with very carefully controlled amounts of electrolytes. More particularly, a minimal quantity of electrolyte was used so that the cathode did not become inundated. However, too little electrolyte increases the internal resistance of the cell and, therefore, reduces sensitivity and slows response. Hence, greater cell sensitivity was obtained only by carefully controlling the amount of elctrolyte and the porosity of the diaphragm.

The applicant has discovered that materials of which the anode is made and the materials of which the cathode is made must be carefully selected to insure that parasitic chemical reactions do not occur which would produce by-products that might tend to short circuit the diaphragm. It has been a problem in the past that undesirable materials have been used which produce such chemical reactions and by-products. In addition, some combinations of materials produce undesirable thermal electromotive forces and galvanic potentials. In this respect, copper, silver and iridium are undesirable materials.

SUMMARY OF THE INVENTION

It is an object of the present invention to provide a method and means of construction of a galvanic cell for measuring minute quantities of oxygen by which at least some of the above-mentioned problems and/or disadvantages of prior techniques are avoided.

It is another object to provide a method and means of construction of an improved galvanic cell for measuring minute quantities of oxygen.

It is another object of the present invention to provide a method and means of construction of a galvanic cell for measuring minute quantities of oxygen wherein the quantity of electrolyte in the cell is less critical than in the past.

It is another object to provide such a galvanic cell with the ability to absorb more oxygen for its size than the cells in the prior art.

It is another object to provide such a galvanic cell wherein undesired thermal electromotive forces and galvanic potentials are eliminated or at least minimized.

It is another object to provide such a galvanic cell of improved speed and efficiency.

In the present invention, the selected anode material is carried on a metal screen attached to an anode blade of the same metal and the cathode is provided by a porous blanket of the selected cathode material 10 to 15 millimeters thick. The porous, non-conductive, electrolyte retentive material (the diaphragm) between the anode and cathode may be relatively thin compared to the thickness of the cathode and is sandwiched between the anode and cathode in intimate contact with both; and the anode, diaphragm and cathode are tightly pressed together. The cathode conductive lead is a strip of metal between the cathode and the diaphragm and, preferably, extends the length of the contact between the cathode and diaphragm and is made of the same metal as the anode blade.

This assembly of anode, diaphragm and cathode is immersed in an electrolyte, such as KOH, and at the same time the cell is electrically charged with a plus voltage at the cathode and a relatively minus voltage at the anode. When recharged, the cell electrodes are shorted and the assembly is sealed inside an oxygen-free envelope into which gas can be introduced and exhausted from suitable ports in the envelope. The relatively thick layer of cathode material has a greater ability to gather and absorb oxygen introduced into the cell during a test. The location of the cathode conductive lead between the cathode and diaphragm provides for greater speed of reaction of the cell and greater efficiency because the contact area between the anode lead and the cathode lead provided through the cell is greater than would be obtained if the cathode lead were attached to the outside of the cathode.

These and other objects and features of the present invention will appear from the following descriptions of specific embodiments of the invention taken in conjunction with the figures.

DESCRIPTION OF THE DRAWINGS

FIG. 1 is a side view of the anode blade, anode conductive lead and plug that seals the open end of the cell envelope;

FIG. 2 is a front view of the blade;

FIG. 3 is a side view of the blade to which is attached the anode material; FIG. 4 is a front view of the blade to which is attached the anode material;

FIG. 5 is a side view of the anode blade to which is attached the anode material, the diaphragm and the cathode conductive lead;

FIG. 6 is a front view of what is shown in FIG. 5;

FIG. 7 is a side view of the anode blade to which is attached the anode, the diaphragm, the cathode conductive lead and the cathode;

FIG. 8 is a front view of what is shown in FIG. 7; and

FIG. 9 is an enlarged cross-section view of a part of complete galvanic cell assembly in the envelope into which oxygen has been introduced illustrating the galvanic action.

GENERAL DESCRIPTION OF EMBODIMENTS OF THE INVENTION

The method and means of construction of the preferred embodiment of the present invention are illustrated by FIGS. 1 to 8. These figures show progressive stages of assembly of the various parts of the cell and FIG. 9 illustrates in diagrammatic form the operation of this cell as it consumes absorbed oxygen in the measurement of the amount of the absorbed oxygen. Additional steps performed in the preparation of the materials and parts that are assembled are also described. The assembly, illustrated by FIGS. 1 to 8, is a generic assembly and need not be limited to the specific materials, preparation of materials or dimensions that are described herein relative to the preferred embodiment.

As shown in FIGS. 1 and 2, the anode blade 1 is a rigid piece with an integral conductive anode lead 2 that is inserted through the stopper 3. The anode blade and lead are preferably a single piece of metal, but if made of two pieces, both pieces should be made from the same metal. Strips of anode material 4 and 5, each about the same size as the blade, are attached to the blade, one on each side, so that they are in intimate contact with the blade. The anode strips may be fastened to the blade by tying with nylon string. For example, unwaxed nylon dental floss may be used.

Next, a strip of diaphragm material as long as the blade and about six times as wide is wrapped around the blade over the anode material as shown in FIG. 5 and secured in place by the same kind of nylon string 6. Then, the cathode conductive lead 9, which may be a wire, is wrapped around the diaphragm from top to bottom and the bottom end of this wire is inserted through the plug. This wire may be inserted through the plug 3 by first inserting a hollow needle 20 through the plug and then threading the wire through the needle and removing the needle. Next, the cathode sheet or blanket 11 is folded over the assembly as shown in FIG. 7 and is securely tied in place by nylon string 12. This secured assembly is next emersed in a suitable electrolyte and the cell is charged by connecting positive voltage to terminal 9 and negative voltage to terminal 2. In a typical case, charging takes several hours and when it is completed, the two electrodes 2 and 9 are shorted together. Immediately thereafter, the excess electrolyte is removed by pressing the assembly between absorbing towels and immediately thereafter the assembly is inserted into envelope 13 into which the stopper fits at one end and the cell is purged of oxygen and within 24 hours the assembly is ready for use to measure small amounts of oxygen introduced into the envelope.

FIG. 9 is an enlarged cross-section view of the end of the assembly, viewed from the side showing the symmetrical sandwich arrangement and the wrap-around technique. This figure also illustrates diagrammatically the operation of the cell. The diaphragm material 7 and cathode contain electrolyte. Then, when oxygen is introduced into the envelope, it is quickly absorbed into the cathode through the cathode surface 11'. The absorbed oxygen is immediately ionized in the electrolyte absorbed by the cathode and the resultant oxygen ions migrate through the diaphragm to the anode, oxidizing the anode material and releasing electrons at the anode. The released electrons flow through an external electric circuit and increase the potential on terminal 2.

If a load resistor is used in series with the cell, as in the prior art, an electric potential accumulates across the anode and cathode. This potential causes electrolysis and increases the response time and decreases the accuracy of the cell. However, if the cell is connected to a "virtual ground" detection circuit, as described in my copending patent application with William H. Morong III, entitled "Measurement of Oxygen In A Fluid Sample,", now U.S. Pat. No. 4,042,465, no potential can build up across the electrodes and the electrolysis reaction does not occur. Hence, electrical equipment, such as described in said copending application, can be provided that feeds controlled current to the cell to maintain a substantially zero potential across the cell and a measure of that current is a measure of the amount of the absorbed oxygen that is consumed (the oxygen that oxidizes the anode material).

PREPARATION OF PARTICULAR MATERIALS

The preferred anode and cathode materials are cadmium and graphite, respectively. The cadmium anode material is carried on a screen of nickel wire. Nickel powder is sintered onto the nickel screen and then electroplated with cadmium. This is available commercially under the trade name Jungner material and is sometimes called cadmium bearing nickel screen. The two strips of anode material 4 and 5 are cut from the commercially available Jungner material, each ⅜ inch wide and about 6 inches long. They are bound to the blade 1 which is a plate of nickel ⅜ inch wide by a little over 7 inches long with the anode lead 2 extending from the center of one end of the plate.

Small crystals of cadmium on the nickel screen are preferred, because small crystals provide a greater total surface area of cadmium. Small crystal growth can be encouraged by repeatedly charging and discharging the cadmium. For example, before assembly, each anode strip is charged at a current density of at least a half an ampere per square inch of the screen. Furthermore, the charging current is preferably an asymmetrical square wave with a duty cycle of approximately 80%. When commercially available Jungner material is used, the charging and discharging current density is preferably about 1 ampere per square inch of the screen and the charging current wave form is a square wave of 4 milliseconds on and 1 millisecond off. As a precaution, after several charge and discharge cycles, the cadmium is brought to a state of about 50% charge and then the anode strips 4 and 5 are attached to the blade 1 using, for example, unwaxed nylon dental floss.

The cathode sheet or blanket 11 is preferably a piece of non-woven graphite cloth and measures 1 inch wide, 13 inches long and is about ⅜ inch thick. Before assembly, the graphite sheet is heated to purify it. For example, it is heated to yellow-white heat immediately before assembly.

The diaphragm sheet 7 is a porous, non-conductive, nonreticulated sheet of material suitable for holding the electrolyte. For example, one suitable material is sold commercially under the trade name Pellon. Other well-known plastic materials are porous polyvinyl chloride, polyethlene and cellophane. The sheet of Pellon is about 4 inches wide and about 7 to 8 inches long. Where the Pellon sheet, wrapped around the assembly as already described, extends beyond the blade 1, it may be folded back at the end.

The cathode conductive lead 9 is a nickel wire 15 inches long and about 0.02 inches in diameter and the stopper 3 may be a commercially available stopper made of Neoprene.

The envelope is specially formed of glass, open at one end to accomodate the stopper and equipped with two ports 14 and 15 at either end to accommodate introducing the oxygen to the cell and exhausting the cell, respectively. A technique for extracting oxygen from blood or respired air is described in the above-mentioned co-pending patent application entitled "Measurement of Oxygen in a Fluid Sample."

The assembled cell bound tightly with nylon filiment, such as unwaxed nylon dental floss, is immersed short of the stopper in a 24% solution of KOH, and while immersed, the cell is charged electrically. A relatively positive voltage is applied to the cathode electrode 9 and negative voltage is applied to the anode electrode 2 of sufficient magnitude to draw about 150 milliamps for about 16 hours. Then the cell electrodes 2 and 9 are shorted together. Next, the cell is removed from the KOH solution and pressed between absorbing towels to remove most of the KOH. Immediately thereafter, the cell is placed inside the enclosure 13, which may be purged free of oxygen, the stopper is sealed and the ports 14 and 15 are closed. This cell is very conveniently used to measure the oxygen content of a sample of blood or respired air as described in the above-mentioned, copending patent application.

The thick layer of cathode material (blanket 11) which is about twice the thickness of the cathode layers in the prior art, increases the ability to the galvanic cell to gather and absorb oxygen. In addition, the thicker cathode eliminates the necessity of maintaining a precise amount of electrolyte in the cell.

The cell is capable of consuming the oxygen in a 20 microliter air sample and returning to within 5 microamps of its original base current in 150 seconds when the cathode electrode 9 is connected to ground and the anode electrode 2 is maintained at a virtual ground. The peak current drawn by the cell under these conditions is over 3000 microamps and the background level output of the cell when sealed in an oxygen-free environment inside the envelope is less than 2 microamps. Furthermore, the integrated output of the cell should vary less than 1 percent with the repeated addition of a fixed quantity of oxygen.

The cell assembly procedure and technique and the specific construction of the cell and procedures described herein provide a cell of relatively high sensitivity and efficiency, not unduly sensitive to the amount of electrolyte absorbed in the cell. Other techniques for applying the principals of the present invention may be employed and changes made in regard to some of the details and still provide an improved cell without deviating from the spirity and scope of the invention as set forth in the appended claims.

What is claimed is:

1. An electrode assembly for detecting and measuring small amounts of oxygen absorbed by the assembly comprising,
   a. a central anode formed of at least one material selected from the group consisting of cadmium, arsenic, bismuth, antimony, lead and ferrous hydrate, said anode providing an anode surface,
   b. a sheet of porous, nonconductive electrolyte retentive material wrapped around the anode in intimate contact therewith,
   c. a porous cathode formed of at least one material selected from the group consisting of carbon, gold and platinum, folded over the electrolyte retentive material in intimate contact at the interface therewith,
   d. an anode conductor at the center of the anode material in intimate contact with said anode material,
   e. a conductive lead extending from the anode conductor and providing an anode terminal,
   f. a cathode conductor between the cathode and the porous, nonconductive, electrolyte retentive material extending throughout said interface in intimate contact with the cathode material and
   g. a conductive lead extending from the cathode conductor and providing a cathode terminal.

2. An electrode assembly as in claim 1 wherein,
   a. the anode, the cathode, the electrolyte retentive material and the anode conductor are arranged in contiguous layers and
   b. the cathode conductor is between the cathode layer and the electrolyte retentive material layer.

3. An electrode assembly as in claim 2 wherein,
   a. the contiguous layers are symmetrically arranged on each side of the central anode conductor, the arrangement of layers on one side of the anode conductor being substantially a mirror image of the arrangement of layers on the other side thereof.

4. An electrode assembly as in claim 3 wherein,
   a. the cathode conductor extends between the contiguous layers of cathode and electrolyte retentive material on both sides of the anode conductor.

5. An electrode assembly as in claim 4 wherein,
   a. the anode conductor is a plate having two ends and the anode conductive lead is continuous with one of said ends and
   b. the electrolyte retentive material on both sides of the anode plate is a single continuous sheet, wrapped around the plate.

6. An electrode assembly as in claim 5 wherein,
   a. the cathode conductor is of sufficient length to extend parallel to the plate on both sides thereof substantially the full lengths of both layers of the cathode on both sides of the plate.

7. An electrode assembly as in claim 4 wherein,
   a. the anode conductor is a plate having two ends and the anode conductive lead is attached to one of said ends and
   b. the cathode extending on both sides of the plate is a single continuous sheet folded over the other end of the plate.

8. An electrode assembly as in claim 7 wherein,
   a. the cathode conductor is of sufficient length to extend parallel to the plate on both sides thereof substantially the full length of both layers of the cathode on both sides of the plate.

9. An electrode assembly as in claim 1 wherein,
   a. the anode is formed of at least one cadmium bearing nickel screen,
   b. the anode conductor is nickel, and
   c. the cathode conductor is nickel.

10. An electrode assembly as in claim 9 wherein,
    a. the cathode is a sheet porous to the electrolyte and the cathode material is graphite.

11. A method of making an electrode assembly for measuring small amounts of oxygen absorbed by the assembly comprising the steps:
    a. providing a metal anode plate;
    b. attaching a metal anode screen bearing an anode material selected from the group consisting of cadmium, arsenic, bismuth, antimony, lead and ferrous hydrate to each side of the anode plate;
c. wrapping a sheet of porous, non-conductive electrolyte retentive material around the metal screen;
d. wrapping a metal wire around the sheet of electrolyte retentive material;
e. wrapping a sheet of cathode material selected from the group consisting of carbon, gold and platinum, around the sheet of electrolyte retentive material;
f. immersing the assembly in an electrolyte solution; and
g. enclosing said assembly in a sealed envelope.

12. A method as in claim 11 and further including the steps of:
a. charging the electrode assembly by connecting to a source of electrical energy while immersed in the electrolyte; and
b. then shorting the anode to the cathode.

13. A method as in claim 11 wherein,
a. the anode material is cadmium.

14. A method as in claim 13 and further including the steps of:
a. before attaching the metallic anode screen bearing the cadmium, charging and discharging the cadmium repeatedly to produce cadmium crystals of reduced size.

15. A method as in claim 13 wherein,
a. the charging and discharging of the cadmium is at current density of at least one half an ampere per square inch of the anode screen.

16. A method as in claim 15 wherein, p1 a. the cadmium is charged and discharged by an assymetrical square wave of current with a duty cycle of about 80%.

17. A method as in claim 16 wherein,
a. the assymmetrical square wave is about 4 milliseconds on followed by 1 millisecond off.

18. A method as in claim 11 wherein,
a. the cathode material is carbon in the graphite form.

19. A method as in claim 18 and further including the step of:
a. before wrapping the sheet of graphite around the sheet of electrolyte retentive material, heating the graphite sheet to purify the graphite.

20. A method as in claim 19 wherein,
a. the graphite sheet is heated to white-yellow heat immediately before assembly.

21. An electrode assembly for detecting and measuring small amounts of oxygen absorbed by the assembly comprising,
a. an anode formed of a screen of inert material having at least a part thereof thinly coated with a material selected from the group consisting of cadmium, arsenic, bismuth, antimony, lead and ferrous hydrate,
b. a porous cathode formed of at least one material selected from the group consisting of carbon, gold and platinum,
c. a porous electrically non-conductive electrolyte retentive material between the anode and cathode in intimate contact with both,
d. the anode, porous electrolyte retentive material and porous cathode are contiguous layers in that order,
e. one side of the electrolyte retentive materials being in intimate contact with the coated part of the anode screen and the other side being in intimate contact with an area of the porous cathode in registration with said coated part of the anode screen, and
f. a cathode conductor between the cathode and electrolyte retentive material, said conductor extending throughout said area of the porous cathode in intimate contact therewith.

22. An electrode assembly as in claim 21 wherein,
a. two coated anode screen areas are provided in registration and facing in opposite directions,
b. the electrolyte retentive material is a sheet of such material wrapped around the anode in intimate contact with both said coated areas thereof,
c. the cathode conductor is wrapped around the electrolyte retentive material, and
d. the cathode is a sheet wrapped around the electrolyte retentive material and cathode conductor in intimate contact with both.

23. An electrode assembly as in claim 22 wherein,
a. the cathode conductor is a wire wound spirally around the electrolyte retentive material.

24. An electrode assembly as in claim 23 wherein,
a. the anode material is cadmium, and
b. the cathode material is carbon.

* * * * *